US005500097A

United States Patent [19]

Yamamoto et al.

[11] Patent Number: 5,500,097

[45] Date of Patent: Mar. 19, 1996

[54] METHOD FOR REMOVING ORGANIC COMPOUND IN WATER

[75] Inventors: Shinji Yamamoto; Kazutoshi Itoyama; Seiichi Fujimaki, all of Kurashiki, Japan

[73] Assignee: Mitsubishi Chemical Corporation, Tokyo, Japan

[21] Appl. No.: 364,996

[22] Filed: Dec. 28, 1994

[30] Foreign Application Priority Data

Dec. 28, 1993 [JP] Japan .................................... 5-349467

[51] Int. Cl.[6] ................................ B01D 3/06; C02F 1/06

[52] U.S. Cl. ................................ 203/11; 203/73; 203/78; 203/79; 203/84; 203/85; 203/88; 210/180; 570/262

[58] Field of Search ................................ 203/14, 10, 11, 203/78, 79, 84, 85, 92, 93, 96, 97, 15–19; 570/262; 210/180

[56] References Cited

U.S. PATENT DOCUMENTS

| | | | |
|---|---|---|---|
| 2,589,212 | 3/1952 | Agapetus et al. | 203/14 |
| 3,488,398 | 1/1970 | Harpring et al. | 570/262 |
| 3,634,200 | 1/1972 | Obrecht et al. | 570/262 |
| 4,057,472 | 11/1977 | Toriya et al. | 203/14 |
| 4,177,111 | 12/1979 | Pieper et al. | 203/14 |
| 4,747,914 | 5/1988 | Schwarzmaier et al. | 203/22 |
| 5,294,303 | 3/1994 | Robbins et al. | 203/14 |

FOREIGN PATENT DOCUMENTS

| | | | |
|---|---|---|---|
| 281181 | 8/1990 | German Dem. Rep. | 570/262 |
| 1685908 | 10/1991 | U.S.S.R. | 570/262 |

OTHER PUBLICATIONS

The Institution of Chemical Engineers, Symposium Series No. 104, 1987, pp. B284–B289, "Distillation and Absorption 1987".

*Primary Examiner*—Wilbur Bascomb, Jr.
*Attorney, Agent, or Firm*—Oblon, Spivak, McClelland, Maier, & Neustadt

[57] ABSTRACT

The present invention provides a method for removing an organic compound in water at a high efficiency by separating an organic compound, particularly such an organic chlorine compound as 1,2-dichloroethane, carbon tetrachloride and chloroform dissolved in water or forming two liquid phases with water from a water phase, by the steps of:

(i) charging water containing an organic compound into a first distillation column for conducting distillation or steam distillation to take the organic compound and water out of the top of the first distillation column and to obtain a bottom liquor containing the organic compound at a lower content from the bottom of the first distillation column, and (ii) charging the bottom liquor of the first distillation column into a second distillation column operated at a pressure lower than that in the first distillation column for conducting distillation, preferably flashing under reduced pressure, to take a gas distillate containing a large amount of the organic compound out of the top of the second distillation column and to obtain a bottom liquor containing the organic compound at such a content as to be lower than the organic compound content in the charged liquor from the bottom of the second distillation column.

9 Claims, 2 Drawing Sheets

2
(B)
(C)
1
3
8
4
6
(A)
(D)
5
7

METHOD FOR REMOVING ORGANIC COMPOUND IN WATER

BACKGROUND OF THE INVENTION

1. Field of the Invention

The present invention relates to a method for removing an organic compound in water, particularly such an organic chlorine compound as 1,2-dichloroethane, carbon tetrachloride or chloroform. More particularly, the present invention relates to a method for reducing an organic compound content in water to such a low level as to be hardly attainable by conventional methods by separating an organic compound including an organic chlorine compound such as 1,2-dichloroethane or others from a water phase by making effective use of heat energy.

2. Discussion of Background

Heretofore, there have been proposed various methods for removing an organic compound in water, such as distillation method, adsorption separation method, activated sludge method and incineration method. Among these methods, steam distillation method has been conventionally conducted for removing an organic chlorine compound azeotropic with water, such as 1,2-dichloroethane, carbon tetrachloride and chloroform.

However, since the solubility of 1,2-dichloroethane or chloroform in water is relatively high, their contents in a bottom liquor obtained after steam distillation can hardly be reduced to a satisfactory level. In order to further reduce the organic compound content to a satisfactory level, it is necessary to use a large-scale apparatus and a large amount of heat energy of steam or the like, and such a large-scale method is not preferable from economical and practical viewpoints.

SUMMARY OF THE INVENTION

The present invention provides a method for removing an organic compound in water, particularly an organic chlorine compound such as 1,2-dichloroethane, carbon tetrachloride or chloroform, by distillation at an efficiency higher than conventional methods without increasing the consumption of heat energy such as steam and the like.

Thus, the present invention provides a method for removing an organic compound in water at a high efficiency by separating an organic compound, particularly such an organic chlorine compound as 1,2-dichloroethane, carbon tetrachloride and chloroform, dissolved in water or forming two liquid phases with water from the water, which comprises:

(i) charging water containing an organic compound into a first distillation column for conducting distillation or steam distillation to take the organic compound and steam out of the top of the first distillation column and to obtain a bottom liquor containing the organic compound at a lower concentration from the bottom of the first distillation column, and (ii) charging the bottom liquor from the first distillation column into a second distillation column operated at a pressure lower than that in the first distillation column for conducting distillation, preferably flashing under reduced pressure, to take a gas distillate containing a large amount of the organic compound out of the top of the second distillation column and to obtain a bottom liquor containing the organic compound at such a concentration as to be lower than the organic compound content in the charged liquor from the bottom of the second distillation column.

DETAILED DESCRIPTION OF THE INVENTION

Figure 1:
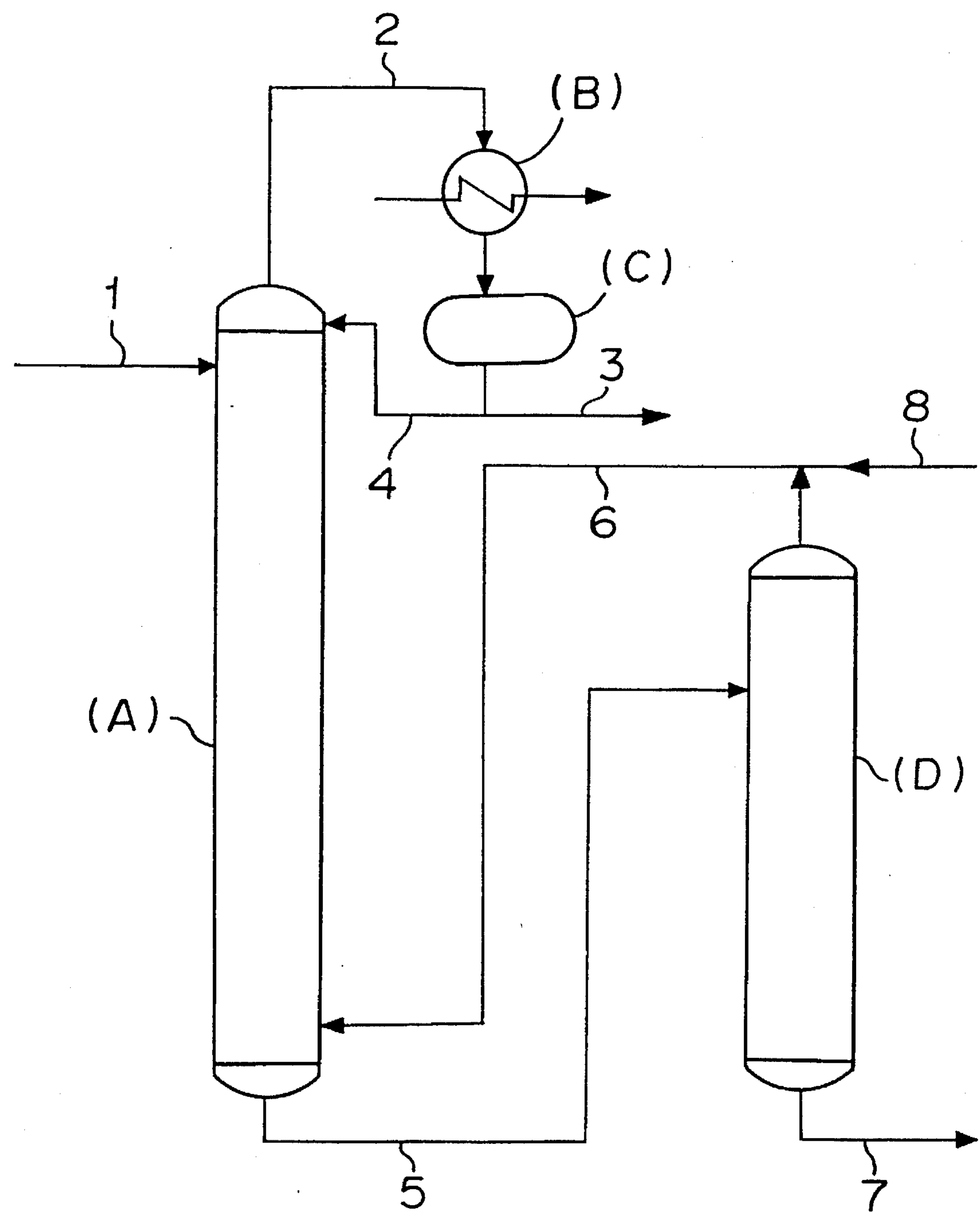
FIG. 1 is a flowchart illustrating an example of an apparatus system used in the present invention.

Hereinafter, the present invention is described in further details.

Water containing an organic compound (hereinafter referred to as "starting liquor") to be treated in accordance with the method of the present invention is water containing an organic compound dissolved in water or forming two liquid phases with water, particularly water containing at least one organic chlorine compound such as 1,2-dichloroethane, carbon tetrachloride and chloroform, the typical example of which includes a waste water discharged in the production of an organic chlorine compound. This-sort of starting liquor forms one liquid phase as a saturated or unsaturated solution of an organic chlorine compound, or forms two liquid phases in which an organic chlorine compound is present exceeding its solubility.

An organic compound to be removed in accordance with the present invention, is dissolved in water or forms two liquid phases with water, and is separable by distillation, or is a compound azeotropic with water which is separable by steam distillation.

The organic compound to be removed in accordance with the present invention preferably has a boiling point in the range of from 40° C. to 100° C. under atmospheric pressure (1 atmosphere), or the organic compound azeotropic with water preferably has an azeotropic point in the range of from 40° C. to 100° C. An organic compound having a boiling point (or azeotropic point) lower than 40° C. is easily separable from water without employing the method of the present invention. On the other hand, an organic compound having a boiling point (or azeotropic point) exceeding 100° C. is hardly separable unless the distillation column is operated at a pressure lower than 100 mmHg, and it is therefore necessary for removing the organic compound having a boiling point (or azeotropic point) exceeding 100° C. to provide a large-scale vacuum apparatus. Thus, an economically advantageous effect of the present invention can not be satisfactorily achieved in the case of removing an organic compound having a boiling point (or azeotropic point) outside the above-mentioned range.

Among organic compounds, an organic chlorine compound is hardly removable by activated sludge method or incineration method, but can be effectively removed by the method of the present invention. Particularly, it is hard to treat water containing at least one member selected from the group consisting of 1,2-dichloroethane, carbon tetrachloride and chloroform by conventional methods. For example, it is very hard to reduce a 1,2-dichloroethane content to less than 100 ppb by weight (ppb=1/1,000,000,000) by conventional methods, but the removal of the organic chlorine compound to such a low concentration can be satisfactorily effected by the method of the present invention.

In the method of the present invention, the above-mentioned starting liquor is charged into a first distillation column where distillation is conducted at an operation pressure (pressure at the top of the distillation column, hereinafter the same) in the range of from a reduced pressure to a pressurized pressure, preferably from 500 mmHg to 2000 mmHg, more preferably at atmospheric pressure, to take a fraction containing an organic compound at a concentration higher than that of a bottom liquor out of the top of the distillation column and to obtain the bottom liquor comprising water as the main component and containing an organic compound at a concentration lower than that of the starting liquor from the bottom of the distillation column.

When an organic compound to be removed is azeotropic with water, it is preferable and effective to conduct steam distillation since the partial pressure of the organic compound to be removed can be easily made lower.

Steam to be blown into the first distillation column where steam distillation is conducted, may be steam separately prepared, but a gas distillate containing steam as the main component obtained from a second distillation column may be advantageously used, thereby largely saving steam required for the steam distillation of the organic compound.

The liquor taken out of the bottom of the first distillation column is charged into the second distillation column.

The second distillation column is operated at a pressure lower than the operation pressure of the first distillation column. Difference in the operation pressures between the two distillation columns is preferably at least 30 mmHg, more preferably at least 60 mmHg, still more preferably at least 90 mmHg, and most preferably at least 150 mmHg, and it is preferable to conduct reduced pressure distillation or reduced pressure flashing in the second distillation column. The operation temperature in the second distillation column is not higher than 99° C., preferably not higher than 98° C., more preferably not higher than 97° C. when the first distillation column is operated under atmospheric pressure. It is usually preferable to make the operation pressure in the second distillation column as low as possible so that the content of the organic compound in the bottom liquor can be made lower, but a large-scale vacuum apparatus is required in order to make the operation pressure still lower. Thus, the operation pressure may be appropriately adjusted depending on the aimed organic compound concentration in the bottom liquor.

There is no special lower limit for the operation temperature, but it is economically preferable to make the operation temperature usually at least 10° C., preferably at least 20° C., at which any additional equipment such as a refrigerating equipment is not necessary.

A gas distillate taken out of the top of the second distillation column is a steam containing an organic compound in a relatively large amount, a part or the whole part of which may be recycled to the first distillation column and used as a steam source for steam distillation to make efficient use of heat energy.

On the other hand, the bottom liquor comprising water as the main component and not containing an organic compound substantially (for example, 1,2-dichloroethane concentration is lower than 300 ppb by weight) can be obtained from the bottom of the second distillation column.

DESCRIPTION OF THE PREFERRED EMBODIMENT

The present invention is further illustrated in accordance with the following embodiments by using Figures and using waste water containing 1,2-dichloroethane, carbon tetrachloride, chloroform and the like produced in the production of an organic chlorine compound such as vinyl chloride as a starting liquor. However, it should be noted that the present invention is by no means restricted to such specific embodiments.

In FIG. 1, a starting liquor containing an organic chlorine compound such as 1,2-dichloroethane, carbon tetrachloride and chloroform is charged into a first distillation column (A) through a starting liquor-charging conduit (1). A typical composition of the starting liquor comprises 0.1 to 3% by weight of 1,2-dichloroethane, 0.01 to 1% by weight of carbon tetrachloride, 0.1 to 2% by weight of chloroform, and minor amounts of high boiling point compounds and water insoluble compounds.

The first distillation column (A) is a packed column or multi-stage column comprising 2 to 10 theoretical stages, and a heating system is a steam-straight run system or a reboiler system. In the first distillation column, distillation, preferably steam distillation, is conducted at a pressure of at least 500 mmHg and at a bottom temperature of at least 89° C. A gas containing a large amount of an organic chlorine compound such as 1,2-dichloroethane, carbon tetrachloride and chloroform is distilled out of the top of the first distillation column through an overhead gas-withdrawing conduit (2) and a heat exchanger (B), and the gas distillate is introduced into a refluxing tank (C) through a distillate-withdrawing conduit (3), from which a part of the gas distillate is taken out to the outside and the remaining part of the gas distillate is recycled into the distillation column (A) through a recycling conduit (4). The ratio of the recycled amount to the distillate amount (recycling ratio) ranges from 0 to 1, and it is advantageous in view of energy if the recycling ratio is smaller.

On the other hand, a bottom liquor containing usually less than 3 ppm by weight of 1,2-dichloroethane and less than 30 ppm by weight of chloroform is taken out from the bottom of the first distillation column, and is charged into a second distillation column (D) through a bottom liquor-withdrawing conduit (5).

The second distillation column (D) is a flash drum or a multi-stage column of 1 to 5 theoretical stages, and is operated at a pressure lower than that in the first distillation column. The pressure difference between the two columns is preferably at least 30 mmHg, more preferably at least 60 mmHg, still more preferably at least 90 mmHg and most preferably at least 150 mmHg. The operation temperature of the second distillation column is less than 99° C., preferably less than 98° C., more preferably less than 97° C. when the first distillation column is operated under atmospheric pressure.

Figure 2:
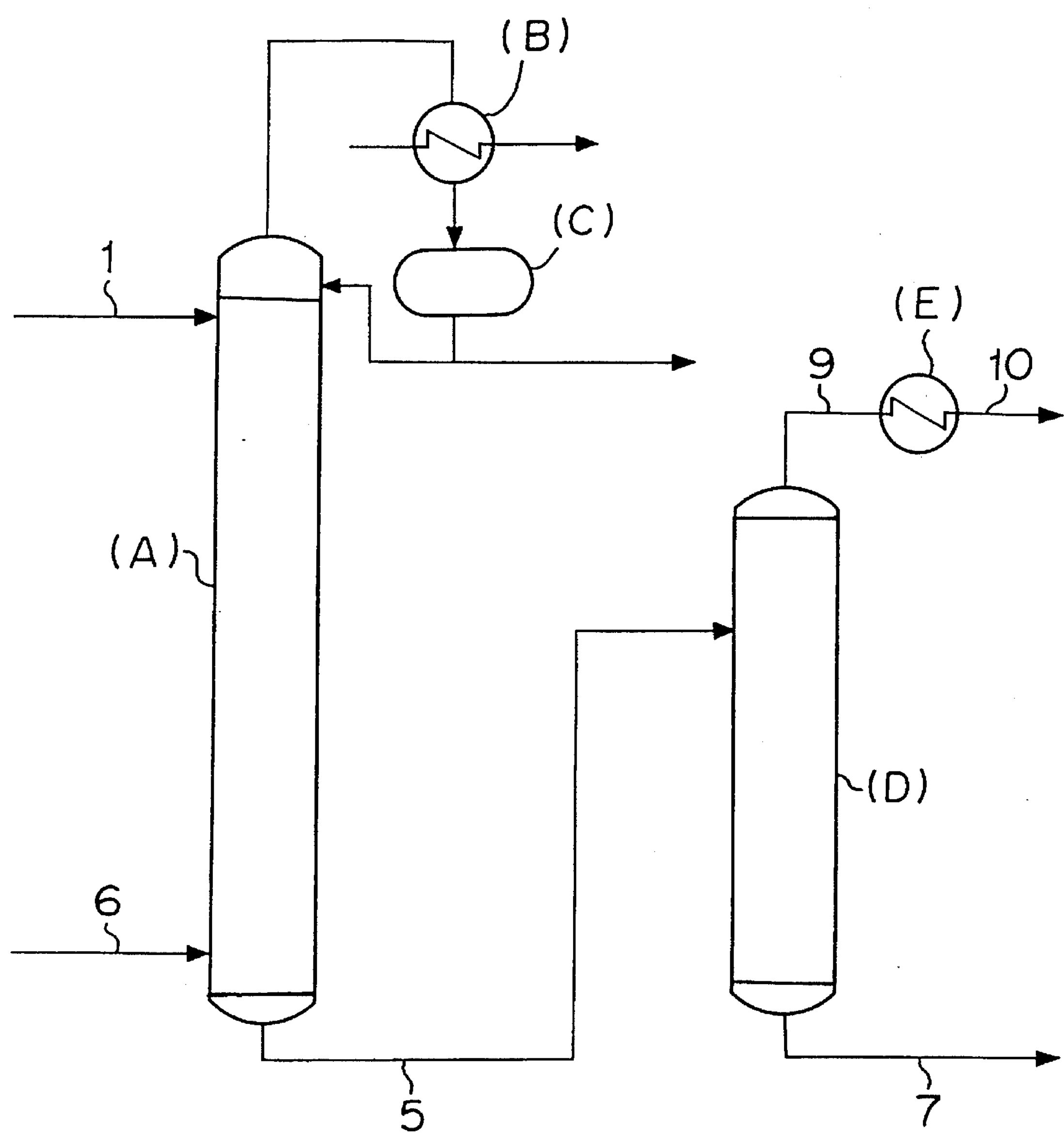
FIG. 2 is a flowchart illustrating another example of an apparatus system used in the present invention.

A gas containing an organic chlorine compound such as 1,2-dichloroethane, carbon tetrachloride, chloroform and the like is distilled out from the top of the second distillation column, and a part or the whole part of the gas distillate is recycled to the first distillation column (A) through an overhead gas-withdrawing conduit (6) to use as a steam for steam distillation in the first distillation column, or the gas distillate may be taken out of the system to the outside through an overhead-withdrawing conduit (9) and a heat exchanger (E) and through a distillate-withdrawing conduit (10) as shown in FIG. 2.

On the other hand, water which does not substantially contain an organic chlorine compound such as 1,2-dichloroethane, carbon tetrachloride, chloroform and the like, is taken out from the bottom of the second distillation column, and this bottom liquor is taken out through a bottom liquor-withdrawing conduit (7). The bottom liquor thus taken out has substantially no fear of causing environmental pollution, and can be reused for various processes.

Now, the present invention will be described in further detail with reference to Examples. However, it should be understood that the present invention is not limited to such specific Examples and that any changes or modifications can be made by those skilled in the art within the spirit and scope of the present invention.

In the Examples, the content of 1,2-dichloroethane, carbon tetrachloride or chloroform was measured in accordance with calibration curve method using a gas chromatograph equipped with a hydrogen flame ionization detector (FID).

EXAMPLE 1

As shown in the flowchart of FIG. 1, water containing 0.52% by weight of 1,2-dichloroethane, 0.164% by weight of chloroform and a minor amount of carbon tetrachloride was charged into a starting liquor-charging inlet provided in the vicinity of the top of a first distillation column (A) having a packed bed of a substantial height of 7 m through a starting liquor-charging conduit (1) in an amount of 16300 kg/hr. On the other hand, a gas including steam (introduced through conduit (8)) in an amount of 1000 kg/hr and an overhead gas distillate taken from a second distillation column was charged into the bottom of the first distillation column through a steam-charging conduit (6), and steam distillation was conducted in the first distillation column at an overhead pressure of atmospheric pressure, at an overhead temperature of 99.8° C. and at a bottom temperature of 100.3° C.

A gas comprising water and organic chlorine compounds such as 1,2-dichloroethane, chloroform, carbon tetrachloride and others was distilled out of the top of the first distillation column in an amount of 1200 kg/hr, and the whole part of the distillate thus obtained was taken out of the system to the outside through a distillate-withdrawing conduit (3).

A majority of 1,2-dichloroethane, chloroform and carbon tetrachloride was taken out from the top of the first distillation column to the outside of the system.

On the other hand, a bottom liquor comprising water as the main component and containing 184 ppb by weight of 1,2-dichloroethane and 1.754 ppm (1754 ppb) by weight of chloroform was taken out from the bottom of the first distillation column through a bottom liquor-withdrawing conduit (5) in an amount of 16860 kg/hr, and was charged into a starting liquor-charging inlet of the second distillation column.

The second distillation column (D) used herein is a flash drum, and reduced pressure flashing operation was conducted at a temperature of 76° C. and at a pressure of 300 mmHg (460 mmHg lower than the pressure used in the first distillation column) to obtain a gas distillate comprising water as the main component and containing 3.95 ppm by weight of 1,2-dichloroethane and 34.50 ppm by weight of chloroform from the top of the second distillation column in an amount of 760 kg/hr, the whole part of which was recycled into the bottom of the first distillation column through an overhead gas distillate-withdrawing conduit (6) of the second distillation column connected with a steam-charging conduit of the first distillation column, thereby using the recycled gas distillate as a steam source for the first distillation column.

On the other hand, a bottom liquor comprising water containing 6 ppb by weight of 1,2-dichloroethane and 208 ppb by weight of chloroform was taken out from the bottom of the second distillation column. Thus, according to the method of the present invention, about 100% of 1,2-dichloroethane and about 99.99% of chloroform could be separated and removed.

EXAMPLE 2

Distillation operation was conducted in the same manner as in Example 1, except that the whole part of the overhead gas distillate from the top of the second distillation column was taken out from the system to the outside as shown in the flowchart of FIG. 2.

A bottom liquor comprising water as the main component and containing 514 ppb by weight of 1,2-dichloroethane and 13.227 ppm by weight of chloroform was taken out from the bottom of the first distillation column in an amount of 16800 kg/hr. The bottom liquor thus obtained was charged into the second distillation column where distillation treatment was conducted to obtain a bottom liquor comprising water as the main component and containing 16 ppb by weight of 1,2-dichloroethane and 1.568 ppm by weight of chloroform in an amount of 16100 kg/hr. In this manner, substantially about 100% of 1,2-dichloroethane and about 99.91% of chloroform were separated and removed.

EXAMPLE 3

Distillation operation was conducted in the same manner as in Example 1, except that water containing 1.8% by weight of 1,2-dichloroethane, 0.8% by weight of chloroform and 0.05% by weight of carbon tetrachloride was used as a starting liquor, and that the operation pressure of the second distillation column was 385 mmHg (375 mmHg lower than that in the first distillation column).

By this operation, water containing 0.895 ppm by weight of 1,2-dichloroethane, 11.686 ppm by weight of chloroform and 0.041 ppm by weight of carbon tetrachloride was obtained in an amount of 16800 kg/hr from the bottom of the first distillation column. The bottom liquor thus obtained was charged into the second distillation column and subjected to distillation treatment therein to obtain a bottom liquor comprising water containing 40 ppb by weight of 1,2-dichloroethane and 1.884 ppm by weight of chloroform from the bottom of the second distillation column in an amount of 16300 kg/hr. In this manner, substantially about 100% of 1,2-dichloroethane, about 99.98% of chloroform and about 100% of carbon tetrachloride were separated and removed.

EXAMPLES 4 to 9

Distillation operation was conducted in the same manner as in Example 1, except that the distillation conditions of the second distillation column were changed as shown in the following Table. The analytical results concerning the contents of 1,2-dichloroethane and chloroform in the second distillation column and others are shown in the following Table, together with those of Examples 1 to 3.

As evident from the results shown in the Table, in Example 4, 459 ppb by weight of 1,2-dichloroethane and 11.07 ppm by weight of chloroform in the bottom liquor of the first distillation column were respectively reduced to about 45% (1,2-dichloroethane) and about 82% (chloroform) by operating the second distillation column at a pressure of only 30 mmHg lower than that in the first distillation column.

Also, it was proved by Examples 4 to 9 that the concentrations of 1,2-dichloroethane, chloroform and carbon tetrachloride in a bottom liquor from a second distillation column (i.e. waste water after treatment) could be controlled by adjusting the pressure in the second distillation column.

COMPARATIVE EXAMPLES 1 TO 4

Steam distillation was conducted in Comparative Examples 1 to 4 without using a second distillation column but using a usual first distillation column only, and 1,2-dichloroethane and chloroform were separated by distillation by varying (increasing) a charged amount of steam. The results thus obtained are shown in the following Table.

The composition of a starting liquor and the operation conditions other than a charged steam amount were the same as those of Example 1.

As these results, it was proved that the result of Comparative Example 1 using 1.5 times amount of steam was equivalent to that of Example 4 in which operation was conducted by making a pressure of the second distillation column 30 mmHg lower than that in the first distillation column, that the result of Comparative Example 2 using 2.5 times amount of steam was equivalent to that of Example 5 in which operation was conducted by making a pressure of the second distillation column60 mmHg lower than that in the first distillation column, and that the result of Comparative Example 4 using 4.5 times amount of steam was equivalent to that of Example 6 in which operation was conducted by making a pressure of the second distillation column 90 mmHg lower than that in the first distillation column. As evident from these results, it is clear that, in the operation of using the first distillation column only, the concentration of 1,2-dichloroethane in a bottom liquor is not satisfactorily reduced even by using a large amount of steam. However, according to the method of the present invention, a concentration of 1,2-dichloroethane can be easily reduced to a low concentration of less than 100 ppb or less than 40 ppb without substantially increasing a steam amount.

Thus, according to the present invention, an organic compound concentration in waste water after treatment can be remarkably reduced by employing a combination of first and second distillation columns and making an operation pressure of the second distillation column lower than that in the first distillation column as compared with a usual separation method by distillation using the same steam amount, and therefore a steam amount used can be largely saved for an operation of reducing the concentration of the organic compound to the same aimed level.

TABLE

| | Starting liquor | | | Bottom liquor of first distillation column | | Distillation conditions of second distillation column and composition of bottom liquor | | | |
|---|---|---|---|---|---|---|---|---|---|
| Unit | Steam kg/h | EDC wt % | $CHCl_3$ wt % | EDC ppb | $CHCl_3$ ppb | Δp mmHg | Temp. °C. | EDC ppb | $CHCl_3$ ppb |
| Example 1 | *1 | 0.52 | 0.164 | 184 | 1754 | 460 | 76 | 6 | 208 |
| Example 2 | 1000 | " | " | 514 | 13227 | 460 | 76 | 16 | 1568 |
| Example 3 | *1 | 1.8 | 0.8 | 895 | 11686 | 375 | 82 | 40 | 1884 |
| Example 4 | " | 0.52 | 0.164 | 459 | 11070 | 30 | 98.9 | 205 | 9118 |
| Example 5 | " | " | " | 419 | 9615 | 60 | 97.8 | 127 | 6839 |
| Example 6 | " | " | " | 384 | 8369 | 90 | 96.5 | 86 | 5172 |
| Example 7 | " | " | " | 259 | 3979 | 260 | 88.7 | 20 | 1173 |
| Example 8 | " | " | " | 206 | 2362 | 390 | 81.2 | 9 | 400 |
| Example 9 | " | " | " | 134 | 704 | 660 | 51.5 | ND | 20 |
| Comparative Example 1 | 1500 | 0.52 | 0.164 | 213 | — | — | — | — | — |
| Comparative Example 2 | 2500 | " | " | 125 | — | — | — | — | — |
| Comparative Example 3 | 3500 | " | " | 102 | — | — | — | — | — |
| Comparative Example 4 | 4500 | " | " | 90 | — | — | — | — | — |

*1: 1000 kg/h + overhead gas distillate of second distillation column
EDC: 1,2-Dichloroethane (boiling point: 83.7° C., azeotropic point (with water): 71.6° C.)
$CHCl_3$: Chloroform (boiling point: 61.2° C., azeotropic point (with water): 56.1° C.)
Δp: Operation pressure difference between first distillation column and second distillation column
ND: Less than detectable lower limit (less than 4 ppb)

What is claimed is:

1. A method for purifying water by removing an organic compound therefrom, which comprises:

(i) introducing water containing an organic compound having a boiling point of from 40° C. to 100° C. or having an azeotropic boiling with water of from 40° C. to 100° C. dissolved in said water or forming a liquid phase with said water into a first distillation column, distilling the organic compound and water out of the top of said first distillation column and to obtain a first bottom liquor containing said organic compound in a lower amount than present in said water introduced into said first distillation column from the bottom of said first distillation column, and (ii) introducing said first bottom liquor of said first distillation column into a second distillation column operated at a pressure lower than that in the first distillation column, distilling a vapor overhead containing a larger amount of the organic compound than present in said first bottom liquor out of the top of said second distillation column and to obtain a second bottom liquor containing the organic compound in a lower amount than present in said first bottom liquor introduced into said second distillation column.

2. The method according to claim 1, further comprising introducing steam into said first distillation column.

3. The method according to claim 1, further comprising introducing the vapor overhead produced in the second distillation column and taken out of the top of the second distillation column into the bottom of the first distillation column.

4. The method according to claim 1, wherein the second distillation column is operated at such a pressure as to be at least 30 mmHg lower than the operation pressure of the first distillation column.

5. The method according to claim 1, wherein said lower pressure in the second distillation column is obtained by flashing.

6. The method according to claim 1, wherein the organic compound is azeotropic with water and has an azeotropic boiling point in the range of from 40° C. to 100° C.

7. The method according to claim 1, wherein the organic compound is at least one organic chlorine compound.

8. The method according to claim 7, wherein the organic chlorine compound is at least one member selected from the group consisting of 1,2-dichloroethane, carbon tetrachloride and chloroform.

9. The method according to claim 1, wherein the organic compound is present in an amount of at most about 6% by weight.

* * * * *